United States Patent
Andrews et al.

(10) Patent No.: US 6,541,036 B1
(45) Date of Patent: Apr. 1, 2003

(54) TREATMENT OF TUMORS WITH OLIGONUCLEOTIDES DIRECTED TO INSULIN-LIKE GROWTH FACTOR-I RECEPTORS (IGF-IR)

(75) Inventors: David W. Andrews, Philadelphia, PA (US); Renato L. Baserga, Ardmore, PA (US); Mariana Resnicoff, Buenos Aires (AR); David Abraham, Wynnewood, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/374,712

(22) Filed: Aug. 13, 1999

Related U.S. Application Data

(63) Continuation of application No. 08/864,641, filed on May 29, 1997, now Pat. No. 6,312,684
(60) Provisional application No. 60/096,354, filed on Aug. 13, 1998, and provisional application No. 60/113,599, filed on Dec. 24, 1998.

(51) Int. Cl.$^7$ .......................... A61K 35/12; A61F 13/00; A61F 2/00; C12N 5/02; C07H 21/04
(52) U.S. Cl. ...................... 424/573; 424/572; 424/422; 424/424; 424/93.1; 536/23.1; 514/44; 435/320.1; 435/325
(58) Field of Search .................. 514/44; 435/320.1, 435/325; 424/93.1, 572, 573, 422, 424; 536/23.1

(56) References Cited

U.S. PATENT DOCUMENTS

| | | | |
|---|---|---|---|
| 4,736,866 A | 4/1988 | Leder et al. .................... 800/1 |
| 4,873,191 A | 10/1989 | Wagner et al. ........... 435/172.3 |
| 5,077,059 A | 12/1991 | Mishima et al. ............. 424/573 |
| 5,139,941 A | 8/1992 | Muzyczka et al. ........ 435/172.3 |
| 5,173,414 A | 12/1992 | Lebkowski et al. ...... 435/172.3 |
| 5,252,479 A | 10/1993 | Srivastava ............... 435/235.1 |
| 5,262,308 A | 11/1993 | Baserga ..................... 435/69.1 |
| 5,272,082 A | 12/1993 | Santoli et al. ........... 435/240.2 |
| 5,354,674 A | 10/1994 | Hodgson ................ 435/172.3 |
| 5,354,678 A | 10/1994 | Lebkowski et al. ...... 435/172.3 |
| 5,399,346 A | 3/1995 | Anderson et al. ........ 424/93.21 |
| 5,460,831 A | 10/1995 | Kossovsky et al. .......... 424/493 |

FOREIGN PATENT DOCUMENTS

| | | |
|---|---|---|
| WO | WO 91/17253 | 11/1991 |
| WO | WO 92/22486 | 10/1994 |
| WO | WO 96/14746 | 5/1996 |
| WO | WO 97/18241 | 5/1997 |
| WO | WO 97/37010 | 10/1997 |
| WO | WO 99/23259 | 5/1999 |

OTHER PUBLICATIONS

Restifo et al. (1993) J. Immunother., vol. 14, 182–190.*
Branch (1998) Antisense & Nucleic Acid Drug Development, vol. 8, 249–254.*
James (1991) Antiviral Chemistry & Chemotherapy, vol. 2 (4), 191–214.*
Vogelstein et al. (1993) Trends in Genetics, vol. 9(4), 139–142.*
Lahm, H. et al., "Growth Inhibition of Human Colorectal Carcinomas by a Monoclonal Antibody Directed Against the IGF–1 Receptor," *Eur. J. Cancer,* 1991, 27(Suppl. 3), Abstract No. 11.053.
Pietrzkowski, Z. et al., "Roles of Insulinlike Growth Factor 1 (IGF–1) and the IGF–1 Receptor in Epidermal Growth Factor–Stimulated Growth of 3T3 Cells", *Mol. Cell Biol.,* 1992, 12(9), 3883–3889.
Pietrzykowski, Z. et al., "Constitutive Expression of Insulin– like Growth Factor 1 and Insulin–like Growth Factor 1 Receptor Abrogates All Requirements for Exogenous Growth Factors", *Cell Growth & Diff.,* 1992, 3, 199–205.
Pietrzykowski, Z. et al., "Inhibition of Growth of Prostatic Cell Lines by Peptide Analogues on Insulin–like Growth Factor 1," *Cancer Res.,* 1993, 53, 1102–1106.
Pietrzykowski, Z. et al., "Autocrine Growth of Cells Overexpressing the Human IGF–1 and IGF–1 Receptor Genes," *Federal of American Society for Experimental Biology,* 75th Annual Meeting, Atlanta, GA, 1991, Part 3, Abstract No. 7268.
Rohlik, Q. et al., "An Antibody to the Receptor for Insulin––like Growth Factor 1 Inhibits the Growth of MCF–7 Cells in Tissue Culture," *Biochem. Biophys. Res. Commun.,* 1987, 149(1), 276–281.
Shapiro, D. N. et al., "Antisense–mediated reduction in insulin–like growth factor–1 receptor expression suppresses the malignant phenotype of a human rhabdomyosarcoma," *Cancer Res.,* Eighty–Third Annual Meeting, 1992, 33, Abstract No. 2112.
Wickstrom, E. et al., "Antisense DNA Methylphosphonate Inhibition of C–MYC Gene Expression in Transgenic Mice," *FASEB J.,* 75th Annual Meeting, Atlanta, GA, 1991, Part 2, Abstract No. 6218.
Resnicoff, M. et al., "Regression of C6 rat brain tumors by cells expressing an antisense insulin–like growth factor I receptor RNA," *J. Exp. Therap. Oncol.,* 1996, 1, 385–389.
Resnicoff, M. et al., "Antitumor effects elicited by antisense–mediated downregulation of the insulin–like growth factor I receptor (Review)," *Int. J. Mol. Med.,* 1998, 1, 883–888.

(List continued on next page.)

*Primary Examiner*—Anne M. Wehbe'
(74) *Attorney, Agent, or Firm*—Woodcock Washburn LLP

(57) ABSTRACT

A method of inducing resistance to or regression of tumor growth comprising placing tumor cells in culture in vitro or ex vivo supplemented with a pro-apoptotic agent for a period of time, transferring the tumor cells into a diffusion chamber, thereby producing a cell-containing chamber, inserting the chamber into a human for a therapeutically effective time, thereby inducing resistance to or regression of tumor growth.

15 Claims, 7 Drawing Sheets

OTHER PUBLICATIONS

Barry, M.A., et al., "Activiation of Programmed Cell Death by Cisplatin, Other Anticancer Drugs, Toxins and Byperthermia", *Biochem Pharmacol*, 1990, 40, 2353–2362.

Baserga and Rubin, "Cell Cycle and Growth Control", *Crit. Rev. Eukaryot. Gene Expr.*, 1993, 3, 47–61.

Becker et al., "Proliferation of human malignant melanomas is inhibited by antisense oligodeoxynucleotides targeted against basic fibroblast growth factor", *EMBO J.*, 1992, 8(12), 3685–3691.

Brown, "Gene Therapy 'Oversold' By Researchers, Jounalists", *Washington Post*, Dec. 8, 1995, pp. 1 and A22.

Bursch, W., et al., "Determination of the length of the histological stages of apoptosis in normal liver and in altered hepatic foci of rats", *Carcinogenesis*, 1990, 11, 847–853.

Buttyan, R., et al., "Induction of the TRPM–2 Gene in Cells Undergoing Programmed Death", *Mol. Cell Biol.*, 1989, 9, 3473–3481.

Conley, "Transplantation of nervous system tumors in diffusion chambers", *J. Neurosurg.*, 1974, 41, 332–338.

Coppola et al., "A Functional Insulin–Like Growth Factor I Receptor is Required for the Mitogenic and Transforming Activities of the Epidermal Growth Factor Receptor", *Mol. Cell. Biol.*, 1994, 14, 4588–4595.

Goldring and Goldring, "Cytokines and Cell Growth Control", *Crit. Rev. Eukaryot. Gene Expr.*, 1991, 1, 301–326.

Harrington et al., "c–Myc–induced apoptosis in fibroblasts is inhibited by specific cytokines", *EMBO J.*, 1994, 13, 3286–3295.

Kaufmann, S.H., "Induction of Endonucleolytic DNA Cleavage in Human Acute Myelogenous Leukemia Cells by Etoposide, Camptothecin, and Other Cytotoxic Anticancer Drugs: A Cautionary Note", *Cancer Res.*, 1989, 49, 5870–5878.

Kolata, "In the rush toward gene therapy, some see a high risk of failure", *The New York Times*, Jul. 25, 1995, p. C3.

Lange et al., "IL–4 and IL–5–Dependent Protective Immunity to Onchocerca Volvulus infective Larvae in BALB/cBYJ mice", *J. Immunol.*, 1994, 153, 205–211.

Lanza et al., "Xenogeneic Humoral Responses to Islets Transplated in Biohybrid Diffusion Chambers", *Transplantation*, 1994, 57, 1371–1375.

Marshall, "Gene Therapy's Growing Pains", *Science*, 1995, 269, 1050–1055.

Martin et al., "Development of an in Vitro Assay for the Survival of Cells Suspended from BA1112 Rat Sarcomas", *Eur. J. Cancer Clin. Oncol.*, 1983, 19, 791–797.

Miller et al., "Gene Transfer and Antisense Nucleic Acid Techniques", *Parasitology Today*, 1994, 10(3), 92–97.

Preston et al., "Regulation of Apoptosis by Low Serum in Cells of Different Stages of Neoplastic Progression", *Cancer Res.*, 1994, 54, 4214–4223.

Ray et al., "Ca2+ antagonists inhibit DNA fragmentation and toxic cell death induced by acetaminophen", *FASEB J.*, 1993, 7, 453–463.

Resnicoff et al., "Rat Glioblastoma Cells Expressing an Antisense RNA to the Insulin–like Growth Factor–1 (IGF–1) Receptor are Nontumorigenic and Induce Regression o Wild–Type Tumors", *Cancer Res.*, 1994, 54, 2218–2222.

Resnicoff, M., et al., "Growth Inhibition of Human Melanoma Cells in Nude Mice by Antisense Strategies to the Type 1 Insulin–like Growth Factor Receptor", *Cancer Res.*, 1994, 54, 4848–4850.

Sell et al., "Simian virus 40 large tumor antigen is unable to transform mouse embryonic fibroblasts lacking type 1 insulin–like growth factor receptor", *Proc. Natl. Acad. Sci. USA*, 1993, 90, 11217–11221.

Sell et al., "Effect of a Null Mutationof the Insulin–Like Growth Factor I Receptor Gene on Growth and Transformation of Mouse Embryo Fibroblasts", *Mol. Cell. Biol.*, 1994, 14, 3604–3612.

Trojan et al., "Treatment and Prevention of Rat Glioblastoma by Immunogenic C6 Cells Expressing Antisense Insulin–Like Growth Factor I RNA", *Science*, 1993, 259, 94–97.

Tseng et al., "Antisense oligonucleotide technology in the development of cancer therapeutics", *Cancer Gene Therapy*, 1994, 1(1), 65–71.

Valentinis et al., "The role of the insulin–like growth factor I receptor in the transformation by simian virus 40 T antigen", *Oncogene*, 1994, 9, 825–831.

Wu–Pong, "Oligonucleotides: Opportunities for Drug Therapy and Research", *Pharm. Tech.*, 1994, 102, 104, 106, 108, 110–112, and 114.

Abraham, et al., "Survival and Development of larval Onchocerca Volvulus in Diffusion Chambers Implanted in Primate and Rodent Hosts", *J. Parasitol.*, 1993, 79, 571–582.

Baserga, R., "Oncogenes and the Strategy of Growth Factors", *Cell*, 1994, 79, 927–930.

Cox et al., "Identification of a Peptide Recognized by Five Melanoma–Specific Human Cytotoxic T Cell Lines", *Science*, 1994, 264, 716–719.

D'Ambrosio et al., "A Soluble Insulin–like Growth Factor I Receptor That Induces Apoptosis for Tumor Cells in vivo and Inhibits Tumorigenesis", *Cancer Res.*, 1996, 56, 4013–4020.

Hoelzer, D. et al., "Low–dose Ara–C in the Treatment of Acute Leukemia Cytotoxicity or Differentiation Induction," *Blut*, 1984, 48(4), 233–238.

Huybrechts, M. et al., "The Diffusion Chamber Technique as an in Vivo Assay in Mice for the Effectiveness of Antitumor Agents," *Scand. J. Haem.*, 1979, 23(3), 223–226.

Kawakami et al., "Identification of a human melanoma antigen recognized by tumor–infiltrating lymphocytes associated with in vivo tumor rejection", *Proc. Natl. Acad. Sci. USA*, 1994, 91, 6458–6462.

Lavin, M.F. et al., "Role of protein kinase activity in apoptosis," *Experientia*, 1996, 52(10–11), 979–994.

Lieberthal, W. et al., "Mechanisms of apoptosis and its potential role in renal tubular epithelial cell injury," *Am. Physiol. Soc.*, 1996, 271(3 Part 2), F477–F488.

Mandelbolm et al., "CTL Induction by a tumour–associated antigen octapeptide derived from a murine lung carcinoma", *Nature*, 1994, 369, 67–71.

Resnicoff et al., "The Insulin–like Growth Factor I Receptor Protects Tumor Cells from Apoptosis in Vivo", *Cancer Res.*, 1995, 55, 2463–2469.

Resnicoff et al., "Correlation between Apoptosis, Tumorigenesis, and Levels of Insulin–like Growth Factor I Receptors", *Cancer Res.*, 1995, 55, 3739–3741.

Scher, C.D., et al., "Platelet–Derived Growth Factor and the Regulation of the Mammalian Fibroblast Cell Cycle", *Biochem. Biophys. Acta.*, 1979, 560, 217–241.

Stiles, C.D., et al., "Dual control of cell growth by somatomedins and platelet–derived growth factor", *Proc. Natl. Acad. Sci. USA,* 1979, 76, 1279–1283.

Ullrich, A. et al., "Insulin–Like Growth Factor I Receptor Primary Structure: Comparison with Insulin Receptor Suggests Structural Determinants that Define Functional Specificity", *EMBO J.,* 1986, 5(10), 2503–2512.

Ullrich, A. And Schlessinger, J., "Signal Transduction by Receptors with Tyrosine Kinase Activity", *Cell,* 1990, 61, 203–212.

Zhou–Li, F., et al., "Association of Insulin Receptor Substrate 1 with Simian Virus 40 Large T Antigen", *Mol. Cell Biol.,* 1995, 15, 4232–4239.

Resnicoff, M., et al., "Antitumor effects elicited by antisense–mediated downregulation of the IGF–1 receptor: From the bench to the bedside," *Proceedings of the American Association for Cancer Research Annual Meeting,* 1999, vol. 40, 729, Abstract No. 4816.

* cited by examiner

Summary of Patients at Enrollment

| Patient | sex | age | diagnosis | Disease course intervals (weeks) | KPS | previous treatment |
|---|---|---|---|---|---|---|
| 1 | M | 34 | GBM[1] | 416[3]/8[4]/0[5] | 80 | resection; RT[6]; chemotherapy; re-resection with Gliadel®[7] |
| 2 | F | 56 | Multifocal GBM | 76/52/8 | 80 | resection; RT; SRT[8]; chemotherapy |
| 3 | F | 32 | GBM | 292/104/0 | 70 | resection; RT; SRT; chemotherapy |
| 4 | M | 44 | Multifocal AA[2] | 240/212/6 | 100 | resection; RT; chemotherapy |
| 5 | M | 40 | GBM | 14/2/0 | 90 | resection; RT; emergency re-resection |
| 6 | M | 45 | GBM | 36/4/0 | 70 | resection; RT; re-resection with brachytherapy |
| 7 | M | 58 | GBM | 16/8/0 | 80 | resection; RT |
| 8 | M | 47 | GBM | 32/16/8 (20)† | 80 | resection; RT; re-resection |
| 9 | M | 68 | GBM | 73/48/0 | 70 | resection; RT; SRT boost; re-resection with Gliadel® |
| 10 | F | 33 | AA | 13/4/4 (17)† | 70 | resection; RT |
| 11 | M | 45 | GBM | 133/12/1 (5)† | 70 | resection; RT |
| 12 | M | 34 | AA | 69/8/8 | 90 | resection; RT; Re-resection with Gliadel® |

[1] glioblastoma multiforme (WHO Grade IV glioma); [2] anaplastic astrocytoma (WHO Grade III glioma)
[3] Time elapsed from original diagnosis to current treatment; [4] Time elapsed from last treatment to recurrence; [5] Time elapsed from recurrence to IGF-IR treatment; [6] Radiation therapy; [7] Gliadel® is polifeprosan 20 with Carmustine implant, Rhone-Poulenc Rorer; [8] Stereotactic radiotherapy; † compassionate re-treatment

Post-Treatment Analysis

| Patient # | # of chambers implanted[1] | Descriptive MRI radiographic course | Descriptive clinical course | Clinical Outcome | Histologic assessment of tumor before and after IGF-IR/AS treatment | Protocol-related response/time to response (weeks) |
|---|---|---|---|---|---|---|
| 1 | 9 | Sustained decrease in contrast enhancement with transient improvement in mass effect followed by increase | Neurologic improvement with more fluent speech and KPS improvement to 90 during stable steroid dose. | Survival 17 weeks; autopsy performed; cause of death: tumor progression | Before: viable tumor; After: tumor vessel thrombosis; LI[3] present; loss of endothelial proliferation | Partial response/10 |
| 2 | 7 | Increase in intensity and nodularity of enhancing areas followed by decrease | Stable exam for two months, then progressive right hemiparesis and expressive aphasia during stable steroid dose; followed by taper during 8 week period of clinical stabilization | Survival 19 weeks; autopsy performed; cause of death: tumor progression | Before: viable tumor: After; tumor vessel thrombosis; no LI | Partial response/14 |
| 3 | 10 | Decrease in intensity and nodularity of enhancing areas; followed by local and distal tumor progression | Improvement in right hemiparesis to ambulation with stable steroid dose; then tumor progression with progressive hemiparesis | Survival 10 weeks; autopsy performed; cause of death: tumor progression | Before: viable tumor; After: tumor vessel thrombosis; LI present | Partial response/10 |
| 4 | 7 | Progression of all assessable features assessed except no change in local mass effect or intensity of enhancing area | Progressive right hemiparesis and aphasia despite increasing steroid dose | Survival 6 weeks; autopsy performed; cause of death: pneumonia/tumor progression | Before: viable tumor; After: tumor vessel thrombosis; LI present | Progressive disease |

| | | | | | | |
|---|---|---|---|---|---|---|
| 5 | 10 | Resolution of all assessable features including contrast-enhancement and mass effect | Progressive improvement to KPS of 100 with non-focal exam; occasional partial seizures; off steroids at three months | Alive and well with return to work and athletic activities at 83 weeks follow-up | Before: areas of necrosis not previously seen 1 Mo after RT; After: not assessed | [Complete response][3] |
| 6 | 10 | Increase in intensity, nodularity and size of enhancing area followed by decrease | Stable receptive aphasia on steroid taper for 2 months, then neurologic decline with global aphasia | Survival 16 weeks; autopsy declined | Before: viable tumor; After: not assessed | [Partial response][4] |
| 7 | 10 | Resolution of all assessable features including contrast-enhancement and mass effect by 8 weeks followed by new 1 cm focus of enhancement with rapid progression noted at 45 weeks in the contralateral frontopolar region | Clinical improvement to mild stable dysnomia with KPS of 90; off steroids at three months with return to full activities through 45 weeks follow-up; asymptomatic small distal focus noted at 45 weeks with rapid progression | Survival 50 weeks; autopsy performed; cause of death: distal tumor progression | Before: viable tumor; no LI After (primary focus): After (distal secondary focus): | Complete response/8 |
| 8 | 10/18[2] | Initial decrease in nodular contrast enhancement with simultaneous increase in invasion of deep white matter, followed by decrease in contrast enhancement and nodularity after re-treatment | Stable neurologic exam with KPS of 80 on stable steroid dose; then scan revealing disease progression: retreated on compassionate use basis with stable exam for 6 weeks; basis with MRI revealing tumor necrosis and hydrocephalus; V-P shunt followed by craniotomy and L-P shunt for persistently dilated IVth ventricle | Survival 17 weeks; autopsy performed; cause of death: tumor progression | Before: viable tumor with mitotic figures and endothelial proliferation; After: tumor vessel thrombosis; LI in first and second post-treatment tumor, massive necrosis after re-treatment | Partial response[2]/12 |

Figure 3B

| | | | | | |
|---|---|---|---|---|---|
| 9 | 10 | No change in MRI scan followed by tumor progression | Stable neurologic exam with mild dysnomia for 3 months; then increasing seizures; MRI revealing disease progression; steroids increased | KPS currently 60 on stable increased steroid dose | Before: viable tumor; After; not assessed | Stable disease |
| 10 | 9/16[2] | Increase in local mass effect, size of T2 weighted abnormality, nodularity of enhancing mass, size of enhancing area, and invasion of deep white matter; followed by decrease in all of the above | Neurologic deterioration including right hemiparesis and expressive aphasia at 14 weeks; MRI scan revealed tumor stable but hydrocephalus; V-P shunt; re-treated on compassionate basis with improvement in speech and motor function | Currently has improved speech and mild improvement in right dense hemiparesis at 50 weeks from original treatment | Before: viable tumor with new mitotic figures; After: tumor vessel thrombosis; no LI | Partial response[2]/12 |
| 11 | 10 | Tumor Progression | Stable exam for four months, then neurologic deterioration including right hemiparesis and moderate aphasia; subsequent palliative left temporal lobectomy | KPS currently 40, hospice placement | Before: viable tumor; LI present After: viable tumor; LI present | Progressive disease |
| 12 | 10/10[2] | Tumor Progression followed by improvement | Stable neurologic exam, followed by worsening left hemiparesis, followed by improvement in left motor function on steroid taper after compassionate re-treatment | KPS currently 70 with return to part-time work at 35 weeks follow-up from original treatment | Before: viable tumor; After: viable tumor | Partial response[2]/14 |

1. Based on a maximum yield of viable cells up to 10 chambers; 2. Re-treatment on compassionate use basis; maximum yield of viable cells up to 20 chamber limit; 3. Lymphocytic infiltration (acquired); 4. Patient 5 not scored because response occurred within 2 weeks of radiation therapy; 5. Patient 6 not scored because response occurred within 4 weeks of brachytherapy.

Figure 3C

TREATMENT OF TUMORS WITH OLIGONUCLEOTIDES DIRECTED TO INSULIN-LIKE GROWTH FACTOR-I RECEPTORS (IGF-IR)

CROSS REFERENCE TO RELATED APPLICATIONS

This application is a continuation of U.S. application Ser. No. 08/864,641, filed May 29, 1997 and claims benefit under 35 U.S.C. § 119(e) to U.S. application Ser. No. 60/096,354, filed Aug. 13, 1998, and U.S. application Ser. No. 60/113,599, filed Dec. 24, 1998 each of which are incorporated herein by reference in their entirety.

FIELD OF THE INVENTION

The present application is directed to inducing resistance to or regression of tumor growth in humans using implanted diffusion chambers containing tumor cells treated with oligonucleotides directed to IGF-IR.

BACKGROUND OF THE INVENTION

Traditional methods of treating tumors in mammals include procedures such as, for example, surgical removal of the tumor, injection or implantation of toxic treatments or syngeneic tissue samples, chemotherapy, and irradiation. The ultimate goal of each of these procedures is to reduce the growth of existing tumors, preferably abrogating tumor growth to the point of complete regression, and/or to induce resistance to future tumor growth. These procedures have numerous effects on tumor cells, as well as on non-tumor cells.

Tumors and other neoplastic tissues are known to undergo apoptosis spontaneously or in response to treatment. Examples include several types of leukemia, non-Hodgkin's lymphoma, prostate tumor, pancreatic cancer, basal and squamous cell carcinoma, mammary tumor, breast cancer, and fat pad sarcoma. Several anti-cancer drugs have been shown to induce apoptosis in target cells. Buttyan, et al., *Mol. Cell. Biol.,* 1989, 9, 3473–3481; Kaufmann, *Cancer Res.,* 1989, 49, 5870–5878; and Barry, et al., *Biochem. Pharmacol.,* 1990, 40, 2353–2362, all of which are incorporated herein by reference in their entirety. Certain mildly adverse conditions can result in the injured cell dying by programmed cell death, including hyperthermia, hypothermia, ischemia, and exposure to irradiation, toxins, and chemicals. It should be noted that many of these treatments will also result in necrosis at higher doses, suggesting that mild injury to a cell might induce cell suicide, perhaps to prevent the inheritance of a mutation, while exposure to severe conditions leads directly to cell death by necrosis. However, the death process is difficult to observe due to the rapidity of the process and the reduced amount of inflammation. For these reasons, quantification of apoptosis is often difficult. A method of measuring the duration of the histologically visible stages of apoptosis (3 hours in normal rat liver) and a formula by which to calculate the cell loss rate by apoptosis is set forth by Bursch, et al., *Carcinogenesis,* 1990, 11, 847–853.

Evidence is also rapidly accumulating that growth factors and their receptors play a crucial role in the establishment and maintenance of transformed phenotypes. It is well established that growth factors play a crucial role in the establishment and maintenance of the transformed phenotype. Mouse embryo cells with a targeted disruption of IGF-IR genes cannot be transformed by SV40 T antigen and/or an activated Ha-ras oncogene that easily transform embryo cells generated from their wild-type littermates. Sell, et al., *Proc. Natl. Acad. Sci. USA,* 1993, 90, 11217–11221; Sell, et al., *Mol. Cell. Biol.,* 1994, 14, 3604–3612; Valentinis, et al., *Oncogene,* 1994, 9, 825–831; and Coppola, et al., *Mol. Cell. Biol.,* 1994, 14,, 4588–4595. Expression of an antisense RNA to the IGF-IR RNA in C6 rat glioblastoma cells not only abrogates tumorigenesis in syngeneic rats, but also causes complete regression of established wild type tumors. Resnicoff, et al., *Cancer Res.,* 1994a, 54, 2218–2222 and Resnicoff, et al., *Cancer Res.,* 1994b, 54, 4848–4850. Related to this finding is also the report by Harrington, et al. (*EMBO J.,* 1994, 13, 3286–3295), that IGF-I (and PDGF) protect cells from c-myc induced apoptosis. A decrease in cell death rate in tumors could certainly be an important mechanism for tumor growth. Baserga, *The Biology of Cell Reproduction,* Harvard University Press, Cambridge, Mass., 1985. Cells expressing an antisense RNA to the IGF-IR RNA or cells pre-incubated with antisense oligonucleotides to the IGF-IR RNA completely lose their tumorigenicity when injected in either syngeneic or nude mice. Resnicoff et al., 1994a, 1994b. The injected cells were suspected of undergoing apoptosis or, at any rate, some form of cell death. Dying cells, however, are very difficult to demonstrate, because dying cells, especially in vivo, disappear very rapidly, and one is left with nothing to examine.

The importance of the IGF-IR in the control of cell proliferation is also supported by considerable evidence: 1) many cell types in culture are stimulated to grow by IGF-I (Goldring, et al., *Crit. Rev. Eukaryot. Gene Expr.,* 1991, 1, 301–326 and Baserga, et al., *Crit. Rev. Eukaryot. Gene Expr.,* 1993, 3, 47–61), and these cell types include human diploid fibroblasts, epithelial cells, smooth muscle cells, T lymphocytes, myeloid cells, chondrocytes, osteoblasts as well as the stem cells of the bone marrow; 2) interference with the function of the IGF-IR leads to inhibition of cell growth—which has been demonstrated using antisense expression vectors or antisense oligonucleotides to the IGF-IR RNA; the antisense strategy was successful in inhibiting cellular proliferation in several normal cell types and in human tumor cell lines (Baserga, et al., 1994, supra.); and 3) growth can also be inhibited using peptide analogues of IGF-I (Pietrzkowski, et al., *Cell Growth & Diff.,* 1992a, 3, 199–205 and Pietrzkowski, et al., *Mol. Cell. Biol.,* 1992b, 12, 3883–3889), or a vector expressing an antisense RNA to the IGF-I RNA (Trojan, et al., 1993, supra.). The IGF autocrine or paracrine loop is also involved in the growth promoting effect of other growth factors, hormones (for instance, growth hormone and estrogens), and oncogenes like SV40 T antigen and c-myb, and in tumor suppression, as in the case of WT1. Baserga, et al., 1994, supra. Inducing resistance to tumor growth is also disclosed in, for example, U.S. Pat. No. 5,714,170, which is incorporated herein by reference in its entirety. A review of the role of IGF-IR in tumors is provided in Baserga et al., *Vitamins and Hormones,* 1997, 53, 65–98, which is incorporated herein by reference in its entirety.

Testing agents such as, for example, growth factors and growth factor receptors for their ability to maintain or suppress transformed phenotypes remains difficult. In order to obtain an accurate account of the tumor suppressive ability, testing should be performed in vivo. The present invention provides a method of inducing resistance to or regression of tumor growth with markedly reduced side effects to the patient.

SUMMARY OF THE INVENTION

The present invention is directed to a method of inducing resistance to tumor growth in a human comprising contacting a tumor cell in vitro or ex vivo with an oligonucleotide complementary to IGF-IR, and implanting a diffusion chamber containing the treated tumor cell into the rectus sheath of the human for a therapeutically effective time, thereby inducing resistance to tumor growth.

The present invention is also directed to a method of inducing regression of a tumor in a human comprising contacting a tumor cell in vitro or ex vivo with an oligonucleotide complementary to IGF-IR, and implanting a diffusion chamber containing the treated tumor cell into the rectus sheath of the human for a therapeutically effective time, thereby inducing regression of the tumor.

BRIEF DESCRIPTION OF THE FIGURES

FIG. 1 shows a table summarizing the patients enrolled in the clinical trial.

FIGS. 3A, 3B and 3C show a table showing post-treatment analysis of the patients enrolled in the clinical trial.

DESCRIPTION OF PREFERRED EMBODIMENTS OF THE INVENTION

Figure 2:
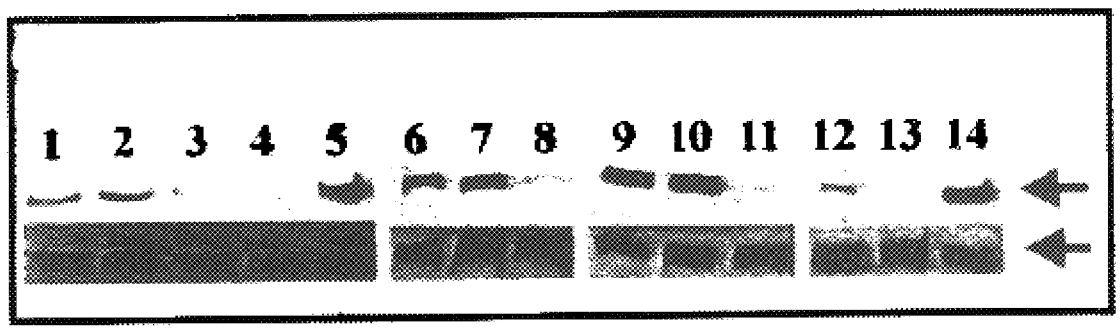
FIG. 2 is a Western blot immunostained with a polyclonal antibody anti-IGF-IR β subunit (upper arrow), then re-stained with a monoclonal antibody to the focal adhesion kinase (lower arrow). Lanes 1: T98G human glioblastoma cells; 2: Patient 1 before treatment; 3: Patient 1+LR 4437-002A (IGF-IR antisense oligonucleotide) at 1 mg; 4: Patient 1+LR 4437-002A at 2 mg; 5: C6 rat glioblastoma cells; 6: T98G human glioblastoma cells; 7: Patient 8 before treatment; 8: Patient 8+LR 4437-002A at 2 mg; 9: T98G human glioblastoma cells; 10: Patient 9 before treatment; 11: Patient 9+LR 4437-002A at 2 mg; 12: Patient 10 before treatment; 13: Patient 10+LR 4437-002A at 2 mg; and 14: T98G human glioblastoma cells.

The present invention is directed, in part, to methods of inducing resistance to tumor growth, or inducing regression of a tumor, in a human comprising treating a tumor cell in vitro or ex vivo with a pro-apoptotic agent, placing the treated tumor cells in a diffusion chamber thereby producing a tumor cell-containing diffusion chamber, and inserting or implanting the tumor cell-containing diffusion chamber into the rectus sheath of the human for a therapeutically effective time thereby inducing resistance to tumor growth or inducing regression of the tumor.

An important advantage of the present invention is that toxic treatments to the tumor cells such as, for example, treatment with irradiation or chemotherapeutic compounds, are performed in vitro or ex vivo thereby eliminating toxicity to the patient. In addition, tumor cells can be placed into culture in a diffusion chamber and the chamber directly implanted into the patient, thus eliminating the possibility of physical spreading of the tumor cells which can be associated with direct injection of tumor cells into a patient.

Human tumors which are treatable with the methods of the present invention can be primary or secondary, benign, malignant, metastatic, or micrometastatic tumors in a human patient. A human patient is an individual who is diagnosed with cancer, an individual who has been diagnosed as having cancer and who is now cancer-free, or an individual who is suspected of having cancer. Tumors treatable with the methods of the present invention include, but are not limited to, melanoma, prostate, ovary, mammary, pancreatic, lungs, colon, and smooth muscle tumors, as well as cells from glioblastoma, bone marrow stem cells, hematopoietic cells, osteoblasts, epithelial cells, fibroblasts, as well as any other tumor cells which undergo apoptosis and induce resistance to or regression of tumor cells.

As used herein, the terms "tumor cell(s)," "tumor(s)," and "cancer cell(s)," as applied to cells which are within a diffusion chamber, are used interchangeably throughout the present application and include, but are not limited to, autografts, allografts, syngeneic, non-syngeneic and xenografts as well as cells derived therefrom. Tumor cells include any type of cell which upon apoptosis induces resistance to tumor growth or induces regression of a tumor including, but not limited to, naturally-occurring tumor cells or tumor cell lines. Tumor cells include, but are not limited to, melanoma, prostate, ovary, mammary, pancreatic, lungs, colon, and smooth muscle tumors, as well as cells from glioblastoma, bone marrow stem cells, hematopoietic cells, osteoblasts, epithelial cells, fibroblasts, as well as any other tumor cells which undergo apoptosis and induce resistance to or regression of tumor cells. Tumor cell lines include, but are not limited to, C6 rat glioblastoma cell line, FO-1 human melanoma cell line, BA 1112 rat rhabdomyosarcoma cell line, B1792-F10 mouse melanoma, B16 mouse melanoma, and CaOV-3 human ovarian carcinoma. Tumorous tissue, tumors, or tumor cells can also be excised from the human patient in which the diffusion chamber will be inserted or from another source which has been cultured in vitro.

Tumor cells used in the methods of the present invention are cultured in vitro or ex vivo in a medium supplemented with a pro-apoptotic agent and subsequently transferred to a diffusion chamber. Alternatively, the tumor cells can be initially cultured in a diffusion chamber and treated with the pro-apoptotic agent therein. Preferably, the diffusion chamber contains tumor cells which are derived from the same type of tumor to which resistance or regression is induced. Alternatively, the tumor cells are placed in a diffusion chamber are of a different type than the tumor to which resistance or regression is induced.

The tumor cells are cultured in vitro or ex vivo and are supplemented with a pro-apoptotic agent for a period of time, preferably 3 to 48 hours, more preferably 24 hours. Prior to culture in vitro or ex vivo, the tumor cells can be gently dissociated with trypsin and subsequently washed prior to implanting in a human. Pro-apoptotic agents which supplement the culture medium of the tumor cells in vitro or ex vivo are preferably agents which induce cell death in vivo. A pro-apoptotic agent, for purposes of the present invention, is an agent which causes death of the tumor cells in the diffusion chamber in vivo such that the cell death has a tumor growth inhibiting effect or tumor regression effect, i.e., a resistant effect or regression effect, on a tumor or tumors or tumor cells in the human in which the diffusion chamber is implanted. Such pro-apoptotic agents include, but are not limited to, nucleic acid molecules, proteins or peptides, non-protein or non-polynucleotide compounds, and physical conditions.

The pro-apoptotic agents used in the methods of the present invention induce cell death, or apoptosis, of the tumor cells in the diffusion chamber in vivo or ex vivo. Apoptosis, for purposes of the present invention, is defined as cell death and includes, but is not limited to, regression of primary and metastatic tumors. Apoptosis is a programmed cell death which is a widespread phenomenon that plays a crucial role in the myriad of physiological and pathological processes. Necrosis, in contrast, is an accidental cell death which is the cell's response to a variety of harmful conditions and toxic substances. Apoptosis, morphologically distinct from necrosis, is a spontaneous form of cell death that occurs in many different tissues under various conditions. This type of cell death typically occurs in scattered cells and progresses so rapidly it is difficult to observe.

Pro-apoptotic agents, or apoptosis-inducing agents, which induce apoptosis of tumor cells in vivo include, for example, nucleic acid molecules. In one embodiment of the invention, the nucleic acid molecule is an oligonucleotide directed against DNA or RNA of a growth factor or growth factor receptor, such as, for example, IGF-IR. Most preferably, the oligonucleotide is directed against DNA or RNA of IGF-IR. The oligonucleotide can be directed to any portion of IGF-IR DNA or RNA. Preferably, the nucleotide sequence of the oligonucleotide includes, but is not limited to, nucleotide sequences complementary to codons 1–309 of IGF-IR (SEQ ID NO:1), comprising either RNA or DNA. The antisense oligonucleotides can also comprise nucleotide sequences complementary to portions of codons 1–309. In addition, mismatches within the nucleotide sequence of the oligonucleotide complementary to codons 1 to 309 are also within the scope of the invention. An oligonucleotide complementary to nucleotides-29 to -24 of the IGF-IR signal sequence (SEQ ID NO:2) comprising DNA or RNA is also within the scope of the present invention. The signal sequence of IGF-IR is a 30 amino acid sequence. Contemplated by this definition are oligonucleotides complementary to the 30 amino acid signal sequence. Alternatively, fragments of oligonucleotides within SEQ ID NO:2 are also contemplated. Additional oligonucleotides of the invention include, but are not limited to, oligonucleotides comprising the following nucleotide sequences: GGACCCTCCTCCG-GAGCC (SEQ ID NO:3), CCGGAGCCAGACTTCAT (SEQ ID NO:4), CTGCTCCTCCTCTAGGATGA (SEQ ID NO:5), CCCTCCTCCGGAGCC (SEQ ID NO:6), TACT-TCAGACCGAGGCC (SEQ ID NO:7), CCGAGGCCTC-CTCCCAGG (SEQ ID NO:8), and TCCTCCGGAGCCA-GACTT (SEQ ID NO:2). The oligonucleotides of the invention can comprise from about 10 to about 50 nucleotides, more preferably from about 14 to about 25 nucleotides, and more preferably from about 17 to about 20 nucleotides.

In another preferred embodiment of the invention, the nucleic acid molecule is a vector which produces an oligonucleotide directed against DNA or RNA of a growth factor or growth factor receptor such as, for example, SEQ ID Numbers 1–9. The nucleic acid molecule complementary to a portion of IGF-IR RNA or DNA is inserted into an appropriate delivery vehicle, such as, for example, an expression plasmid, cosmid, YAC vector, and the like. Almost any delivery vehicle can be used for introducing nucleic acids into tumor cells. Recombinant nucleic acid molecules (or recombinant vectors) include, for example, plasmid DNA vectors, cDNA-containing liposomes, artificial viruses, nanoparticles, and the like. It is also contemplated that vectors expressing the oligonucleotides can be injected directly into the tumor cells.

The regulatory elements of the recombinant nucleic acid molecules of the invention are capable of directing expression in mammalian tumor cells, preferably human tumor cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules of the invention may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions, and the Drosophila HSP70 promoter. Other inducible promoters are known to those of ordinary skill in the art.

Recombinant nucleic acid molecules comprising oligonucleotides of the invention can be introduced into a tumor cell or "contacted" by a tumor cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Forest virus vectors.

In a preferred embodiment of the invention, recombinant vectors comprising oligonucleotides directed to DNA or RNA of IGF-IR, which are described, for example, in Resnicoff, et al. (1994a, 1994b, supra), both of which are incorporated herein by reference, are used. Briefly, plasmid HSP/IGF-IR AS expresses an antisense transcript 309 bp in length directed to IGF-IR RNA, under the control of a Drosophila HSP70 promoter. The hepatitis B polyadenylation signal sequence and a neomycin-resistance gene under the control of the SV40 promoter are present at the 3' termini of the 309 bp IGF-IR fragment. One skilled in the art can readily prepare additional vectors producing any of the oligonucleotides of the invention described herein.

In other embodiments of the invention, the pro-apoptotic agents comprise proteins or peptides such as, for example, associated dominant negative mutants of IGF-IR and MHC class I peptides. Dominant negative mutants of IGF-IR include, for example, soluble IGF-IR, described in D'Ambrosio, et al., Cancer Res., 1996, 56, 4013–4020, incorporated herein by reference, and myristylated C-terminus of IGF-IR (MyCF). MHC class I associated peptides include, for example, Tyr-Leu-Glu-Pro-Gly-Pro-Val-Thr-Ala (SEQ ID NO:9) recognized by melanoma-specific CTL lines (Cox, et al., Science, 1994, 264, 716–719), Leu-Leu-Asp-Gly-Thr-Ala-Thr-Leu-Arg-Leu (SEQ ID NO:10) derived from gp100 and involved in regression of human melanoma (Kawakami, et al., Proc. Natl. Acad. Sci. USA, 1994, 91, 6458–6462), and Phe-Glu-Cys-Asn-Thr-Ala-Gln-Pro-Gly (SEQ ID NO:11) derived from connexin 37 and induces CTL responses against murine lung carcinoma (Mandelbolm, et al., Nature, 1994, 369, 67–71), and Tyr-Leu-Arg-Pro-Gly-Pro-Val-Thr-Ala (SEQ ID NO:14). In addition, inverted D-amino acid analogs of the above-identified peptides, such as Ala-Thr-Val-Pro-Gly-Pro-Glu-Leu-Tyr (SEQ ID NO:12) and Leu-Arg-Leu-Thr-Ala-Thr-Gly-Asp-Leu-Leu (SEQ ID NO:13), are also active. Amino acid substitutions are also contemplated by the present invention. The peptides of the present invention can be made synthetically as is well known to those skilled in the art.

In other embodiments of the invention, the pro-apoptotic agents comprise non-protein or non-polynucleotide compounds such as, for example, chemotherapeutic compounds or synthetic chemical compounds. Preferably, chemotherapeutic compounds include, for example, etoposide, cisplatin, camptothecin, and tumor necrosis factor alpha (TNF-α).

In other embodiments of the invention, the pro-apoptotic agents comprise physical conditions such as, for example, hyperthermia, hypothermia, ischemia, and ionizing irradiation. In embodiments where the tumor cells are exposed to such conditions, the condition is defined for purposes of the present invention as an agent, an apoptosis-inducing agent.

Therapeutically effective doses of the pro-apoptotic agents or apoptotic-inducing agents will be about that of the drugs alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable. The apoptosis-inducing agents of the invention can be used alone or in combination with other apoptosis-inducing agents. Preferably, between about 10 $\mu$g/$10^7$ cells and 100 mg/$10^7$ cells of pro-apoptotic agent is used to treat the tumor cells in vitro or ex vivo. More preferably, between about 100 $\mu$g/$10^7$ cells and 10 mg/$10^7$ cells of pro-apoptotic agent is used. More preferably, between about 1 mg/$10^7$ cells and 5 mg/$10^7$ cells of pro-apoptotic agent is used. Most preferably, about 2 mg/$10^7$ cells of pro-apoptotic agent is used.

The present invention employs the use of a diffusion chamber, in which the cells are contained. Cells are impermeable to a filter fitted on the diffusion chamber; they cannot leave or enter the chamber. The filter on the diffusion chamber has pores in the size range of about 0.25 $\mu$m or smaller, preferably about 0.1 $\mu$m in diameter. Lange, et al., J. Immunol., 1994, 153, 205–211 and Lanza, et al., Transplantation, 1994, 57, 1371–1375, both of which are incorporated herein by reference in their entirety. Accordingly, cell death or apoptosis, can be quantitatively determined. The use of a diffusion chamber can be extended to other cell lines, even non-syngeneic, and even from different species, because of the rapidity with which cell death occurs, about 24 hours, well before any immune reaction could be established.

Diffusion chambers useful in the present invention include any chamber which does not allow passage of cells between the chamber and the patient in which it is implanted, however, permits interchange and passage of factors between the chamber and the patient. The chamber can allow for multiple and sequential sampling of the contents, without contamination and without harming the patient, therefore significantly reducing the number of implantation procedures performed on the patient. A preferred diffusion chamber is described in, for example, U.S. Pat. No. 5,714,170. A representative diffusion chamber comprises a chamber barrel having two ends, a first end and a second end. The barrel may be comprised of one or more rings secured together by non-toxic means. The chamber is fitted at each end with a filter, a first filter and a second filter. The filters are porous to factors such that the factors may pass between the chamber and the patient. The filter pores size can be about 0.25 $\mu$m or smaller, preferably about 0.1 $\mu$m. The filters can be made of plastic, teflon, polyester, or any inert material which is strong, flexible and able to withstand chemical treatments. The filters can be secured in position with rubber gaskets which may also provide a tighter seal. On the barrel portion of the chamber, an opening is provided which can be covered by a cap which is accessed from outside of the patient's body once the chamber is implanted, thus allowing the diffusion chamber to be refilled. The cap can be a screw-on type of self-sealing rubber and fitted to the opening. Sampling of the chamber contents can be performed by accessing the opening by removing the cap on the outside of the patient's body and inserting an ordinary needle and syringe. The chamber can be made of any substance, such as and not limited to plastic, teflon, lucite, titanium, or any inert material which is non-toxic to and well tolerated by humans. In addition, the chambers should be able to survive sterilization. Diffusion chambers are preferably constructed from 14 mm Lucite rings with 0.1 $\mu$m pore-sized hydrophilic Durapore membranes (Millipore, Bedford, Mass.). The diffusion chambers are preferably sterilized with ethylene oxide prior to use.

Tumor cells can be placed in a diffusion chamber in varying amounts. Preferably, about $1\times10^4$ to about $5\times10^6$ cells can be placed in the diffusion chamber. More preferably, about $1\times10^5$ to about $1.5\times10^6$ cells can be placed in the diffusion chamber. More preferably, about $5\times10^5$ to $1\times10^6$ cells are placed in the chamber. Most preferably, about $1\times10^6$ cells are placed in the diffusion chamber. The cells are placed in the diffusion chamber containing media. It is contemplated that any media known to those skilled in the art that supports the growth of cancer cells and which is compatible with a human can be used.

The diffusion chamber can be implanted in a human in the following non-limiting ways: subcutaneously, intraperitoneally, intracranially, or into the rectus sheath, for example. Most preferably, the diffusion chamber(s) is implanted into an acceptor site of the body having good lymphatic drainage and/or vascular supply such as the rectus sheath. The chamber can be removed about 24 to about 30 hours after implantation, if desired. Alternatively, a refillable chamber can be employed such that the diffusion chamber can be re-used for treatments and emptied following treatments. In addition, a plurality of diffusion chambers, preferably between five and 20, can be used in a single patient.

A clinically proven surgical procedure for carrying out the invention in humans involves implantation of diffusion chambers containing the tumor cells treated with the pro-apoptotic agent, such as IGF-IR antisense oligonucleotide, as a suspension. A preferred procedure involves several surgical and/or in vitro tissue processing objectives: 1) harvesting viable tumor tissue, free of fibrinogen and necrosis, from a tumor bed for ex-vivo tumor cell treatment with the IGF-IR antisense oligonucleotide; 2) avoiding excessive or unacceptable operative morbidity, specifically post-operative neurologic deficit related to the procedure; 3) using image-directed tissue selection to achieve these first two objectives; 4) using image-directed surgical resection to maximize the resection of tumor and to minimize residual tumor burden, thereby minimizing any inflammatory process related to either autologous tumor rejection or related to a direct and cytotoxic effect on tumor cells in the post-implantation period; 5) selecting and creating an autologous acceptor site for the generation of the biological response; 6) processing human tissue explants in vitro in order to generate the desired biological response upon re-implantation of the autologous treated tumor cells within 20 hours; 7) in lieu of the previously stated six surgical objectives, processing autologous, homologous, or xenographic cells from established cell lines in order to generate the desired biological response upon implantation of the tumor cells within about 20 hours; and 8) designing a specific implantation protocol for all of the above cell preparations to generate the resistance to or regression of tumor growth.

Successful clinical trials have applied the present invention to human brain tumors known as glioma. Certain tumors, such as brainstem glioma, or deep, and/or multiple brain metastases, are surgically inaccessible and no tissue can be safely harvested in these patients. In such cases where tumors are surgically inaccessible, homologous (human but not host) cell lines, xenographic (non-human) established cell lines, or homologous human primary cell cultures can be utilized as a source to induce the resistance to or regression of tumor growth. To avoid or prevent the complication of deep venous thrombosis, the prophylactic use of low molecular weight heparin is recommended to carry out the present invention. The following examples are illustrative but are not meant to be limiting of the invention.

EXAMPLES

Example 1

General Implantation Protocol

Diffusion chambers comprising either autologous implants of harvested tumor cells or established autologous, homologous, or xenographic cell lines treated with antisense IGF-IR oligonucleotides are implanted into a human in order to induce resistance to or regression of tumor growth. All such tumor cells have been treated with IGF-IR antisense oligonucleotides ex vivo. Use of IGF-IR antisense is made to target the IGF-IR in host tumor cell explants in vitro and to commit the tumor cells to undergo apoptosis in vivo. The targeted pre-treated cells are committed to undergo apoptosis in vivo and subsequently generate biological response modifiers which induce resistance to or regression of tumor growth.

A preferred embodiment comprises a combination method involving in vitro followed by in vivo procedures. First, this method targets IGF-IR in tumor cells in vitro. Tumor cells with decreased levels of IGF-IR are encapsulated in the diffusion chambers and implanted in vivo in the patient (i.e. subcutaneously, within the rectus sheath, intracranially, or in any other host location considered acceptable for implantation). Cells with decreased levels of IGF-IR undergo apoptosis in the diffusion chambers and release diffusible biological response modifiers which are believed to cause the elimination of human malignant brain tumors in the host patient.

One of two surgical protocols is preferably utilized to carry out the present invention with respect to primary and metastatic brain tumors. In a preferred protocol, a craniotomy is employed for tumor resection and autologous cell implantation. Another protocol utilizes no craniotomy but requires the implantation of autologous cell lines, homologous cell lines, or xenographic cell lines in patients.

First, autologous tissue is harvested utilizing a surgical method for glioma. Viable tumor tissue is harvested from the tumor bed (target between 0.5 to 2 grams; a minimum of 500 mg is usually adequate) for ex vivo tumor cell treatment with IGF-IR antisense DNA. It is an objective of this protocol to avoid excessive or unacceptable operative morbidity, specifically post-operative neurologic deficit related to the procedure. Image-directed tissue selection is utilized to achieve viable tumor tissue harvest and to avoid excessive or unacceptable operative morbidity. Surgical resection is also image-directed to maximize tumor resection, to minimize residual tumor burden, and to minimize subsequent inflammatory effects related to autologous tumor rejection in the post-transplantation period. An autologous acceptor site is selected, such that the acceptor site is appropriate for implantation of the diffusion chamber and for the diffusion of the biological modifier. Human tissue explants are processed in vitro to generate the desired biological response upon re-implantation of the autologous treated tumor cells. The re-implantation protocol is designed to generate the biological response modifier trigger in humans.

The patient is first prepared for craniotomy with placement of fiducial coordinates on the scalp. These fiducials will serve as surface registration points for MRI-based intra-operative image guidance. The patient is then taken to the MRI scanner where gadolinium is infused, and image sets in all three orthogonal planes are obtained. The obtained image sets are suitable for the intra-operative image guidance computer software to be utilized in the operating room. Use of gadolinium or similar contrast agents serves to create a tissue plane marker where viable acceptor tumor tissue cells are located. The image-directed localization of a viable tumor plane is key to a successful cell harvest for processing.

Once the imaging phase is complete, the patient is taken to the operating room and prepared for craniotomy. Prophylactic antibiotics are infused intravenously, as are agents to minimize cerebral edema, including steroids and mannitol with lasix. The head is immobilized in three-point head pin fixation and the infrared LED reference block is applied to the head pin fixation device with attention to the orientation of the reference block to the infrared camera. The reference block is positioned for both an unobstructed link to the camera and for sufficient distance from the operative field for unobstructed operative access. A frameless viewing wand is then registered to the scalp fiducials until an acceptable ($\leq 1.5$ mm) registration error is obtained. The fiducial markers are removed and 40 scalp points are registered to ensure accurate registration over the entire operative field. The registration is checked on the computer screen by moving the wand over the scalp in all three orthogonal planes.

Prior to craniotomy, a preferred site for implantation (e.g. the abdomen) is preferably examined and prepared. For example, a preferred mode would include an incision just superolateral to the umbilicus. Other sites, designated above, would also be acceptable. In this case, a four centimeter transverse incision is made with a #10 blade after infiltration with 1% Lidocaine. The wound edge is retracted with a self-retaining retractor to minimize tissue margin disruption during pocket preparation. Sharp dissection with Metzenbaum scissors is performed, and the rectus sheath is exposed, with careful attention to hemostasis with electrocautery. Utilizing toothed forceps and Metzenbaum scissors, the rectus sheath is incised parallel to the skin incision, thereby exposing the rectus abdominus muscle. A series of interconnected pockets are established utilizing blunt finger dissection in the cephalad and caudal extent of the wound between the rectus muscle and the sheath to allow subsequent implantation of up to 10 diffusion chambers, with each chamber measuring 1.8 cm in diameter. Following sub-rectus sheath tunneling, the wound is copiously irrigated with Bacitracin solution in normal saline, is closed in a single layer with a running 3-0 Nylon suture, and is appropriately dressed. Once the acceptor pocket has been initially formed, the craniotomy is performed using the wand to define an accurate scalp and bone flap, if necessary, and standard sterile technique is utilized to prepare the operative field for surgery.

After infiltration with 1% Lidocaine, the scalp is incised with a #10 scalpel blade and the scalp reflected with towel clips. The bone plate is removed, if necessary, with a combination of an acorn Midas Rex dissecting tool followed by the B-1 dissector with footplate. Pre-existing bone plates are removed as appropriate. Prior to opening dura, four peripheral bone fiducials are made with the B-1 dissector to serve as registration points for the viewing wand during tumor resection. The dura is then opened, preferably in a cruciate fashion, utilizing a #15 scalpel blade and Gerald forceps, thereby exposing the cortical surface.

Tumor sample resection then proceeds utilizing intra-operative image guidance. The computer monitor displays on a split screen each orthogonal plane, as well as a fourth view which features an axis at right angles to the viewing wand. Cortisectomy is performed with bipolar electrocautery and a #9 or #11 Frazier sucker, utilizing the wand at each point to direct accurate sampling of the tumor bed. The viable tumor bed margin is featured on the monitor as an area of contrast enhancement. When viable tumor tissue is registered and judged clinically to be acceptable for oligonucleotide pre-treatment (reducing harvest of necrotic debris, inflammatory reaction, and fibrinogen), bayoneted tumor forceps are utilized to harvest tissue for frozen section histopathological confirmation. When viable neoplastic tissue is confirmed, preferably a minimum of 500 mg of tumor tissue is harvested. Every effort is made to harvest viable tissue free of clot and necrotic debris to improve the success of subsequent effective disaggregation and viable cell plating.

After sample harvest, additional tumor debulking is performed until a judged gross total or near-total resection is achieved utilizing image guidance. An aggressive resection is judged to be important to minimize any post-implantation inflammation secondary to autologous tumor rejection.

When satisfied that an effective quantity of tissue has been obtained and an appropriate resection performed, the resection cavity is inspected for any residual bleeding. Bleeding is controlled first with thrombin-soaked cotton balls. Subsequently bleeding is controlled with bipolar electrocautery. When adequate hemostasis is achieved, the resection cavity is lined with thrombin-soaked surgicel. The dura is closed with 4-0 interrupted and running sutures, and the bone plate is re-affixed with a titanium plating system. The scalp is closed in two layers: the galea with 2-0 vicryl interrupted buried sutures and the scalp with either 3-0 nylon or staples.
Preparation of Cells and Incubation of Cells with IGF-IR Antisense DNA, Days One and Two Tumor tissue samples from the operating room are immediately sent for ex vivo processing. Under sterile conditions, the viable tumor margin tissue is gently disaggregated first with a scalpel. Disaggregation is completed with collagenase and protease treatment. Single cell suspension is obtained after passage through a series of gradually decreasing internal diameter needles. Finally, the cells are washed and plated in culture medium supplemented with 10% serum (e.g. fetal calf or fetal bovine).

The cells are allowed to attach for four to six hours. The cells are carefully washed and treated with up to 2 mg of IGF-IR antisense oligonucleotide in a final volume of 20 ml of serum-free medium to avoid exposure to nucleases present in the serum. The oligonucleotide treatment ranges from a minimum of six hours to a maximum of ten hours. The oligonucleotide treatment dose has been established for $1 \times 10^7$ cells. Proportionately more oligonucleotide can be utilized for more cells. For example, up to 3.6 mg of IGF-IR is used in 36 ml of serum-free medium for 18 million cells.

Following the overnight treatment, the cells are harvested and washed carefully. The cells are re-suspended in phosphate-buffered saline (calcium and magnesium-free), and they are placed in the diffusion chambers to a volume of 200 $\mu$l/chamber and a density of $1 \times 10^6$ cells/chamber. This volume/concentration relationship is important to avoid cell death due to hypoxia. In one embodiment, the chambers are irradiated with 5 Gy just prior to implantation to comply with FDA regulations. Another preferred embodiment does not include irradiation. The chambers consist of small Lucite rings measuring 1.4 cm in outer diameter and 0.8 cm in height, with a hydrophilic membrane at each end. The membranes have a 0.1 $\mu$m exclusion limit which impedes the exit or entry of intact cells and allows the diffusion of soluble factors.
Surgical Implantation of Diffusion Chambers, Day 2

On the second post-operative day, the abdominal acceptor site is prepared for diffusion chamber implantation. The timing of this procedure relative to the harvest of the autologous tumor cells is non-obvious and critical. Tumor cells with a targeted IGF-IR are committed to undergo apoptosis under anchorage-independent conditions, such as those in vivo. To avoid the situation where the tumor cells treated with antisense IGF-IR oligonucleotides undergo apoptosis in the diffusion chambers before implantation in the rectal sheath of the patient, a time window of an hour (maximum) has been established between harvest of tumor cells and implantation of diffusion chambers. The time window between cell harvest and re-implantation of the autologous treated tumor cells, which generate the biological signal, preferably should not exceed one hour in order for the peak of the triggering process to occur in vivo. Preferably, the cell harvest and re-implantation of pre-treated cells is performed within as small a time window as possible.

At bedside, the patient is prepared for the procedure; the patient is sedated with 10 mg of Versed, and 1 g of Ancef antibiotic is infused for wound infection prophylaxis. The previously prepared abdominal acceptor site is exposed using standard sterile technique, and 0.5% Sensorcaine is injected into the abdominal incision. Utilizing Metzenbaum scissors, the acceptor site is opened, thereby exposing the rectus sheath which was incised the previous day. Excessive residual bleeding or presence of fibrinous exudate is to be avoided as fibrin may interfere with signal generation and thereby reduce the effectiveness of the procedure. Care is taken once again to control any source of hemorrhage, however small, with a portable heat cautery unit. Any residual fibrin material is removed with copious irrigation with a Bacitracin solution in normal saline. Up to 10 sterile diffusion chambers, each with a volume of 200 µl of tumor cell suspension, are implanted in the previously described rectus sheath pockets. The biological dosimetry includes implantation of $1 \times 10^6$ cells/chamber in 10 chambers for a maximum of $1 \times 10^7$ cells. The diffusion chambers are implanted so the broad membrane side is flat against the rectus abdominus muscle in all cases. The orientation of the chambers is critical to biologically effective transmission of the triggering signal. Selection of this mode, which includes the rectus abdominus muscle as an acceptor site, is important because the lymphatic drainage of this area proceeds via the inguinal lymph nodes to the peri-aortic nodes, which, in turn, drain into the thoracic duct. This pathway of drainage permits diffusible substances derived from the transduced cells to encounter peripheral lymphoid tissue via regional lymph nodes, which are approximately three centimeters from the implantation site.

The rectus sheath is re-approximated with 2-0 vicryl interrupted sutures to secure the diffusion chambers in the flat orientation. The acceptor site is closed with a running 3-0 nylon interlocking suture and is appropriately dressed.

In the first four patients treated with this protocol, a high rate of deep venous thrombosis occurred, possibly attributable to this treatment. Therefore, an addition to the protocol is the use of subcutaneously injected low-molecular weight heparin (fractionated heparin or LOVENOX®) at 40 mg a day. The LOVENOX® is continued as a daily subcutaneous injection for three months.

Surgical Removal of Diffusion Chambers, Day 3

At bedside, the patient is prepared for the procedure of surgical removal of the diffusion chambers. The patient is sedated with 10 mg of Versed, and 1 g of Ancef antibiotic is infused for wound infection prophylaxis. The previously prepared abdominal acceptor site is exposed and prepared with standard sterile procedure. The site is draped, and 0.5% Sensorcaine is injected into the abdominal incision. Utilizing Metzenbaum scissors, the wound is opened, thereby exposing the rectus sheath which was loosely approximated at bedside the previous day. The sterile diffusion chambers are retrieved from the rectus sheath pockets and taken back to the laboratory where they are carefully examined. Specifically, the integrity of the membrane is inspected, and the contents of each chamber are noted for the presence of fibrinogen. The volume recovered from each chamber is determined, and this volume should be same as the original recorded volume. The cellular contents of each chamber are carefully examined, and the rate of viable cell recovery is quantitated. The rectus sheath is reapproximated with 2-0 vicryl interrupted sutures, and the superficial fascia is reapproximated with 2-0 vicryl interrupted horizontal mattress sutures. The skin is reapproximated with an interrupted vertical mattress suture utilizing 3-0 Nylon, and the wound is then appropriately dressed.

Example 2

Implantation of Autologous Cell Lines, Homologous Cell Lines, or Xenographic Cell Lines Surgical candidates for this protocol are not candidates for craniotomy for tumor removal. An example of patients in this group would include patients with brainstem gliomas-tumors often diagnosed radiographically without biopsy due to the dangerous location of these tumors. The surgical paradigm utilized is the same as that described for days two and three.

Day One

On day one, an appropriate cell line is selected and pre-treated according to the same specifications for the freshly harvested autologous samples. The in vitro incubation period and dose of oligonucleotide will also remain the same as for the harvested autologous samples described in detail above.

Post-Implantation Surveillance for Both Groups

After removal of the chambers, surveillance of the patient begins. Routine vital signs and serial neurologic examinations proceed as per routine with standard post-craniotomy patients. MRI scans with and without gadolinium are performed at the first and second post-operative weeks and at each month thereafter.

Additional Details of the Method

In a preferred embodiment of the invention, twelve preferred steps are performed. Image guided craniotomy (1) is performed to resect tumor. The tumor is removed and placed in phosphate-buffered saline (2). Subsequently, tumor tissue is transferred to a petri dish, where the tumor is comminuted into fine pieces with scalpels (3). Disaggregation is continued by enzymatic digestion and single cells are plated in a T-25 tissue culture flask; after 4–6 hours, once the cells have attached, they are incubated with 2 mg of antisense DNA to the IGF-IR in a final volume of 20 ml of serum-free medium for a minimum of six hours (4). Then, cells are detached and transferred to a 15 ml conical tube for several washes (5). Next, the cells are encapsulated in diffusion chambers (6). Before implantation, the cells encapsulated in the diffusion chambers are irradiated with 5 Gy of radiation (7). Cells encapsulated in diffusion chambers are surgically implanted into the rectus sheath of a patient (8), and apoptosis occurs in vivo within 20 hours. Then the chambers are removed from the patient's rectus sheath, and the wound is permanently closed (9). The chambers are opened, and the cells are recovered (9). Subsequently, the cells are transferred to an Eppendorf tube (10). Next, cells are washed (11), and the cells recovered from the diffusion chambers are analyzed for viability by trypan blue exclusion and they are quantitated in a hemocytometer (12).

The details of Day 1 of the procedure are as follows. Tumor tissue from the operating room is transported in a 50 cc conical tube to a BL-2 facility. In the BL-2 facility, the tumor is washed to eliminate red blood cells, and it is transferred to a petri dish and finely minced with scalpels in PBS (1). Cells are transferred to a 1 5ml tube and washed in PBS (2). Then, cells are transferred to a petri dish and dissociated with repeated cycles of enzymatic digestion (3). Next, cells are transferred to a 15 ml conical tube and washed (4). The cells are plated in a T-25 tissue culture flask and allowed to attach (5).

Attachment is required before IGF-IR antisense DNA is added to the incubation medium of 2 mg of IGF-IR antisense DNA in a final volume of 20 ml of serum-free medium for a minimum of six hours. On Day 2, cells are detached with trypsin; and the cells are transferred to a 15 ml conical tube and washed carefully (1). The effect of trypsin is stopped by adding medium supplemented with 10% serum; $10^6$ cells suspended in 200 µl are loaded in each diffusion chamber, and the diffusion chambers are then irradiated with 5 Gy of radiation (2).

On Day 3, diffusion chambers are harvested from the patient's abdomen. Each diffusion chamber is opened and cell contents are removed with an Eppendorf pipette (1). Cells are then transferred to a 1 ml Eppendorf tube and washed (2). The cells are counted in a hemocytometer (3). Cells recovered from the diffusion chambers are re-plated into a T-25 tissue culture flask to assess viability (4).

Observations in Patients Participating in a Phase I Study

The observations in 12 patients participating in a Phase I study are presented. As described above, for each patient craniotomy was performed and an abdominal acceptor site was prepared for chamber implantation. Tumors resected at surgery were disaggregated in a BL-2 facility and attached cells in culture were incubated overnight with an IGF-1R antisense oligonucleotide. Within 24 hours of surgery, up to $10^7$ treated cells were encapsulated in diffusion chambers, non-lethally irradiated, and implanted for an additional period of 24 hours. After chamber retrieval, patients were followed with serial MRI and clinical examinations.

Following antisense treatment, IGF-1R levels in the treated cells dropped to $\leq 10\%$ as determined by Western blotting. Following 24 hour implantation, less than 2% of the antisense treated cells could be recovered. At follow-up, 6 out of 10 evaluable patients revealed partial or complete radiographic and clinical responses. When compassionate re-treatment responses were included, 8 treatment responses were observed. Other than deep venous thrombosis in the first four patients, no other treatment-related side-effects were noted.

This treatment was well-tolerated and yielded a high rate of radiographic and clinical responses. Additionally, histologic observations in post-treatment tumor samples supported treatment-related effects. These data indicate that a non-toxic systemic treatment effect is achieved utilizing this paradigm.

Patients and Methods

This protocol was reviewed and approved by the FDA and the Institutional Review Board at Thomas Jefferson University. Patients with a diagnosis of WHO Grade III or IV glioma who had failed conventional therapies including radiation therapy were enrolled. A total of twelve adult patients, 9 males and 3 females (ages 32 to 68 years, FIG. 1) were enrolled. Four patients had anaplastic astrocytomas and 8 had glioblastoma, and one patient in each group had multifocal disease. Mean time interval between initial diagnosis and this treatment intervention was 122 weeks. Tumor recurrence was associated with clinical symptoms in 9 patients and was documented by surveillance MRI in all 12 patients.

All patients underwent MRI-based image-guided tumor resections as previously described. Where necessary, intraoperative speech and/or motor corticography was performed to preserve function of eloquent cortex. Prior to craniotomy, an abdominal acceptor site for chamber implantation was prepared, dividing the rectus sheath and establishing interconnected pockets between the rectus muscle and the sheath.

During image-guided resection, viable tumor tissue was confirmed by frozen section, and sent to a BL-2 facility for subsequent disaggregation and treatment. Tumor samples were gently disaggregated first with a scalpel and then by enzymatic digestion under sterile conditions. Cells were plated in compete culture medium (DMEM supplemented with 10% fetal bovine serum, penicillin, streptomycin, and glutamine). When the cells attached, they were carefully washed and shifted to serum-free medium (DMEM supplemented with 1 µM ferrous sulfate and 0.1% BSA fraction V, and treated with an IGF-IR antisense oligonucleotide. An 18-mer phosphorothioate oligodeoxynucleotide (GGACCCTCCTCCGGAGCC; SEQ ID NO:3) targeting the IGF-IR RNA and starting 6 nucleotides downstream from the initiating methionine was used. This antisense oligodeoxynucleotide was synthesized by Lynx Therapeutics (Hayward, Calif.), Lot #LR4437-002A, the same Lot as previously described. After a minimum six hour incubation with a dose of 2 mg antisense/$10^7$ cells, the cells were harvested, carefully washed with PBS, calcium and magnesium-free, and placed in the diffusion chambers at a density of $10^6$ cells/200 µl/ chamber. The chambers are small Lucite rings (1.4 cm in diameter with a 0.1 m pore-sized hydrophilic membrane at each end. They allow the passage of soluble factors (such as nutrients or peptides) impeding the exit or entry of intact cells.

On the first post-craniotomy day, the abdominal acceptor site was opened at bedside for diffusion chamber implantation. A time window was selected so that tumor cells treated ex vivo with IGF-1R antisense oligodeoxynucleotide were detached, encapsulated in the chambers and non-lethally irradiated (5 Gy) at the same time the acceptor site was opened. After local anesthesia and antibiotic prophylaxis, the rectus sheath pockets were exposed and up to 10 sterile diffusion chambers were implanted.

On the second post-craniotomy day, the diffusion chambers were retrieved from the rectus sheath pockets and the wound closed. The chambers were transported to a BL-2 facility for analysis after recovery. Post-implantation surveillance included serial clinical and MRI examination.

Compassionate Re-Treatment

Because of the observed anti-tumor effects, three patients who failed initial treatment with IGF-IR antisense were re-treated with a higher biological dose. With FDA approval, the allowable number of chambers was increased to 20 at $10^6$ cells/chamber and maintained the dose of antisense at 2 mg/$10^7$ cells during ex vivo incubation.

Efficacy, Specificity, and Biosafety of the Treatment Paradigm:Ex vivo Assessments Prior to Chamber Implantation To control for the biological activity of the antisense oligodeoxynucleotide, both efficacy and specificity of IGF-1R targeting were assessed. The efficacy of the antisense oligodeoxynucleotide on IGF-IR targeting was determined by measuring the effects on IGF-1R expression at the protein level by Western blotting (see FIG. 2, upper panel). When excess tissues were available, samples were analyzed (N=6) and revealed the presence of IGF-1R with a $\geq 90\%$ reduction of IGF-1R levels after IGF-1R antisense treatment (FIG. 2, upperpanel). The specificity of the antisense oligodeoxynucleotide targeting was determined by ruling out effects on the expression of other tyrosine kinase receptors at the cell surface, such as the focal adhesion kinase (see FIG. 2, lower panel).

The absence of adventitious agents in the autologous tumor cells prior to implantation was confirmed by the use of commercially available kits, including Gram (Fisher Diagnostics) and mycoplasma staining kits (Sigma Chemicals).

Ex vivo Assessments-after Chamber Retrieval

Integrity of the diffusion chambers was determined by measuring the volume before and after implantation. The volume originally loaded in each chamber was 200 ml and the volume recovered from each of the 146 implanted chambers was 198±2 ml. Cell recovery, determined after 24 hour implantation of the diffusion chambers, was <2% of the original cell number implanted. Meticulous microscopic analysis of the cells recovered from the chambers showed that only tumor cells (and mostly non-viable as indicated by trypan blue staining) could be recovered. No other cell types including lymphocytes, monocytes, macrophages, ordendritic cells could be identified. Also, the presence of GFAP-positive cells (a marker for glioma cells) in samples obtained from the abdominal acceptor site was ruled out.

Enoxaparin Prophylaxis

Based on a higher than expected rate of DVT in the first four patients, a regimen of DVT prophylaxis was established in all subsequent patients. On the first postcraniotomy day, a three month regimen of enoxaparin prophylaxis was initiated which involved a daily 40 mg subcutaneous injection. Non-invasive doppler studies were performed immediately before and after the completion of a 12 week course of enoxaparin treatment.

Response Assessments

All patients underwent serial MRI evaluation using a standard brain imaging protocol consisting of T1 and T2 weighted pre-contrast images and TI weighted postcontrast images in the sagittal, axial, and coronal planes. MRI scans were obtained within 48 hours to document residual tumor at treatment inception. Progression, regression or stability of disease was determined by changes in the assessment of seven image characteristics between serial studies including: (1) local mass effect; (2) size of T2-weighted abnormality (e.g. edema, tumor, radiation change); (3) size of the enhancing area; (4) characteristics of the enhancement (e.g. progression or regression of nodularity); (5) intensity of enhancing area; (6) invasion of the deep white matter tracts; and (7) distal progression. Radiographic evaluation was performed by assessing changes in any of these characteristics when comparable images from serial studies were evaluated. Each imaging characteristic was rated as increased, decreased, or without change. In all cases, MRI comparisons were performed for each patient by one neuroradiologist. The first comparison evaluated changes between an MRI study performed immediately following treatment and a follow-up examination performed approximately 4 weeks after initiation of therapy. Subsequent comparisons evaluated changes at two month intervals and later at three month intervals.

Serial clinical examinations were independently performed by a neurosurgeon and a neurologist. Performance status was assessed according to the Karnofsky performance scale (KPS).

Response was assessed after treatment utilizing the following criteria:

complete response: improvement in all assessable imaging characteristics between serial studies to either complete resolution or to a stable image with features consistent with post-operative and/or radiation changes, with improvement or stability of neurological and general physical examinations, off corticosteroid medication, for at least one month.

partial response: improvement in two or more of assessable imaging characteristics, with improvement or stability of neurological and physical examinations, and a stable or decreasing corticosteroid dose, for at least one month.

stable disease: no significant change in the imaging characteristics between serial studies with improvement or stability of neurological and physical examinations, and a stable or decreasing corticosteroid dose, for at least one month.

progressive disease: An increase in the imaging characteristics between serial studies with deterioration of neurological and physical examinations, and with a stable or increasing corticosteroid dose.

Results

Twelve patients with operable malignant gliomas were safely treated utilizing tumor tissue harvested at craniotomy with a mean follow-up of 67±7 weeks (range 40 to 100 weeks). With the exception of compassionate re-treatment in three cases, these patients received no other treatment while under study except appropriate supportive medical and/or surgical therapy. No treatment-related toxicity was identified, and clinical examinations were supported with normal examinations of complete blood counts, liver function studies, CD4+ and CD8+ counts, ANA, anti-ssDNA and anti-dsDNA antibodies.

Biosafety

In all 12 cases, the cells were assessed prior to implantation and found to be free of adventitious agents, and in the post-implantation period there was no clinical evidence of wound infection (N=12). Where evaluable, no glioma tumor seeding was identified at the implantation sites (N=6). A total of one hundred fifty-six diffusion chambers were implanted (FIGS. 3A and 3B), and no membrane disruptions were noted when recovered. Only autologous tumor cells were recovered, and in all cases <2% of recovered cells were viable, as assessed by trypan blue staining.

The only treatment-related complication seen thus far is the high incidence of deep venous thrombosis (DVT) in the first four patients (Patients 1–4; see FIG. 3A). Subsequently a prophylactic regimen utilizing fractionated low-molecular weight heparin (enoxaparin) was initiated in all protocol patients treated thereafter; no DVTs in 8 of the latter patients have occurred. Both patients retreated on a compassionate basis developed DVTs, one while on enoxaparin, the other following selfdiscontinuation of enoxaparin.

Treatment Response: Clinical and Radiographic Observations

Figure 4:
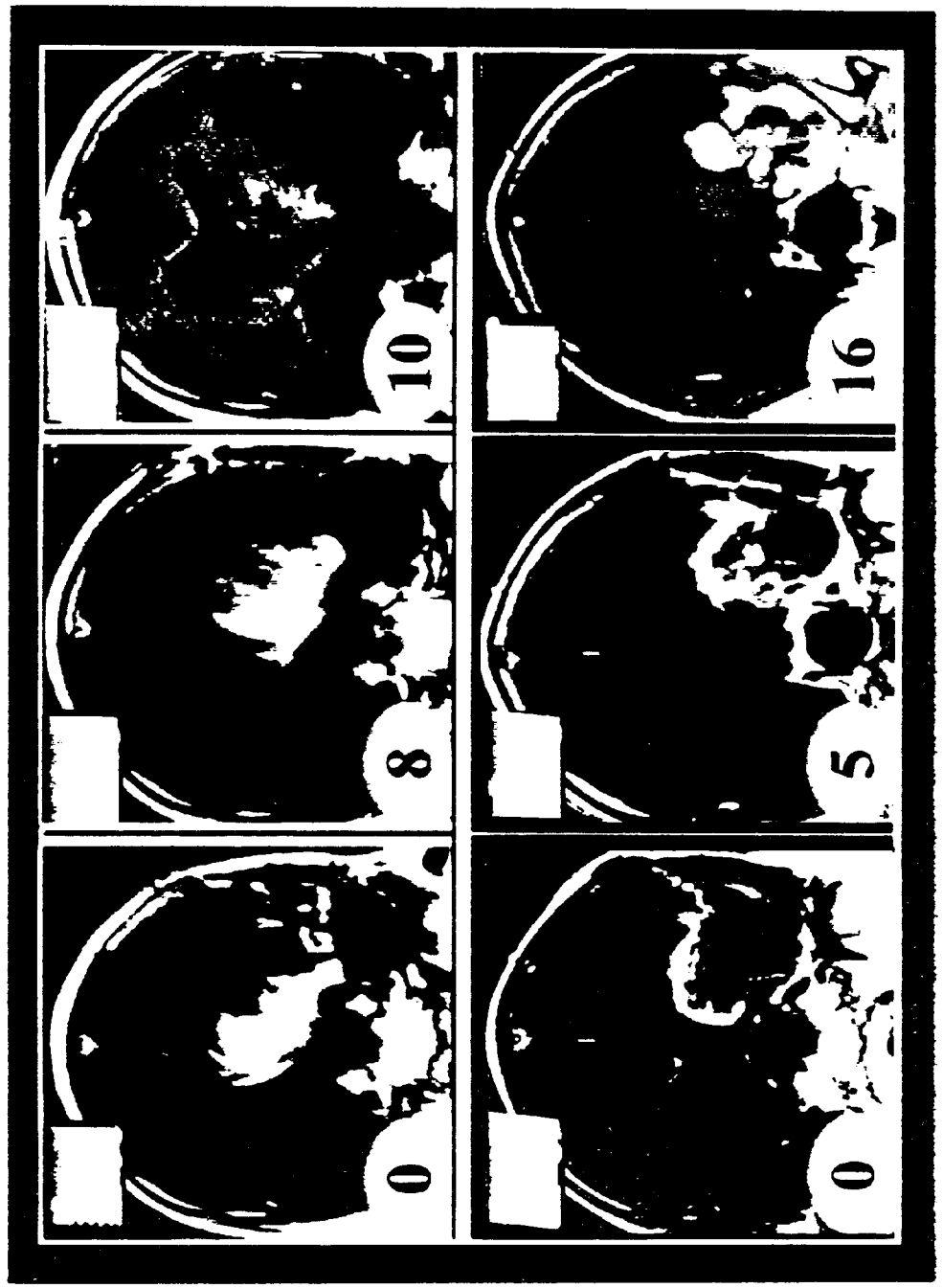
FIG. 4 shows MRI scans of test case (Patient 1, a–c) and case control (d–f) of patients originally diagnosed with malignant glioma originating in the dominant left temporal lobe undergoing lobectomy and radiation therapy with failure and progression into the deep gray matter and ipsilateral frontal lobe. At failure, pathology revealed viable tumor without evidence of radiation necrosis in both case (time 0). The test case received image-guided re-resection and IGF-IR antisense treatment and the case control received image-guided re-resection and GLIADEL® implantation. Numbers in white ovals represent time in weeks after treatment.
Figure 5:
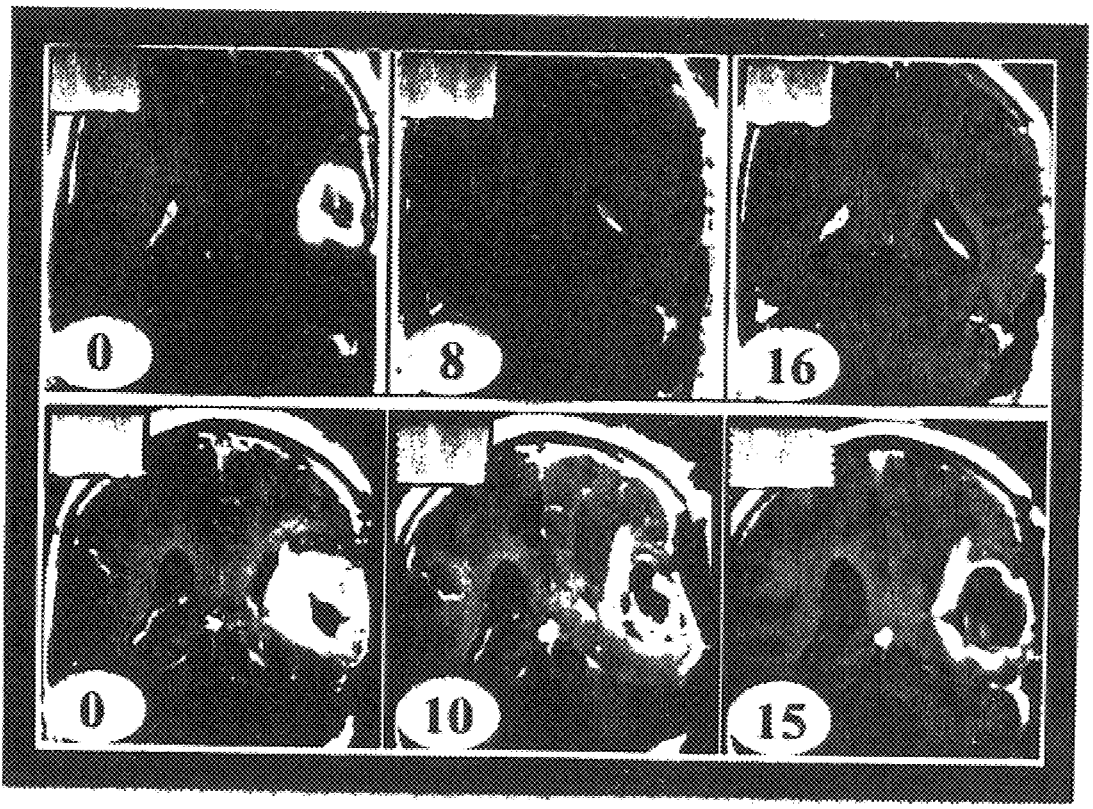
FIG. 5 shows MRI scans of test case (Patient 7, a–c) and case control (d–f) of patients originally diagnosed with malignant glioma originating in the dominant left posterior temporal-parietal region, both with mild receptive aphasias, undergoing resection and radiation therapy with failure and progression into the ipsilateral deep gray matter and frontal lobe. At failure, pathology revealed viable tumor without evidence of radiation necrosis in both case (time 0). The test case received image-guided re-resection and IGF-IR antisense treatment and the case control received image-guided re-resection and GLIADEL® implantation. Numbers in white ovals represent time in weeks after treatment.

In addition to the safety, anti-tumor effects were observed in 4 patients treated once and in an additional 3 patients treated twice, all of whom either improved or stabilized clinically. In all cases, radiographic improvements extended beyond the resection cavity and throughout the ipsilateral and, where applicable, contralateral hemisphere, ans all responses occurred at least two months after a previous conventional treatment judged a failure. An additional two patients improved clinically, one with a sustained complete radiographic and clinical response. A case-control group treated with matched treatments in the same time interval was identified and no comparable anti-tumor effects were observed. In the present series, radiographic improvements occurred by 14 weeks with intervals ranging from eight weeks (Patient 7) to 14 weeks (Patient 2) whereas control cases always revealed persistent tumor characterized by contrast-enhancement. Representative test responses and case controls are shown in FIGS. 4 and 5 and all cases are summarized in FIGS. 3A and 3B. As shown in FIG. 4, a loss of enhancement and mass effect was observed in the test case with corresponding persistence of contrast-enhancement in the case control. In the test case, the patient had clinical improvement which corresponded to the radiographic improvement. As shown in FIG. 5, a loss of enhancement and mass effect with restitution of ipsilateral trigone was observed in the test case but corresponding persistence of contrast-enhancement and effacement of trigone in the case control. In the test case, the patient had clinical improvement with return to all pre-morbid activities which corresponded to the radiographic improvement. This patient succumbed to recurrent disease in the contralateral right frontopolar region and an autopsy has active tumor at the site of recurrence but only scattered tumor cells at the primary site.

In three patients who deteriorated despite some initial radiographic improvement, compassionate retreatment was granted by the FDA and the IRB. After re-treatment, further radiographic loss of nodular enhancement remote from surgical resection occurred in all three with either clinical improvement or stabilization.

Serial tumor tissues in nine cases were analyzed before and after treatment. These observations are summarized in FIGS. 3A and 3B. In 11 of 12 cases, only viable tumor at treatment was observed, without evidence of radiation changes reflected as fibroid necrosis. In two cases of prior GLIADEL® implantation, viable tumor cells were observed contiguous to wafer remnants.

Treatment Response: Histopathologic Observations

Residual viable tumor cells were identified in all post-mortem examinations and in all post-therapy surgical biopsies. Individual cases were observed where the original tumor site either lost endothelial cell proliferation (Patient 1), tumor cell number and pleomorphism (Patient 7), or acquired extensive areas of necrosis (Patient 8 after re-treatment). Microthrombi limited only to tumor-associated blood vessels were identified in 6 of 10 cases for which post-therapy tissue was available. Also, varying degrees of tumor perivascular lymphocytic infiltration were identified in four cases in which no lymphocytic infiltrates were observed in pre-treatment tumor. In brain sections without identifiable tumor cells, inflammation, vasculitis, hemorrhage, necrosis, demyelination, or vessel thrombosis was not identified.

Summary

No systemic toxicity due to this process was noted other than a higher incidence of DVT which prompted initiation of prophylactic anti-coagulation. Radiographic and clinical responses were documented, and these responses cannot be attributed to either surgical intervention or the escalation of steroid dose. In all cases the radiographic improvements were either remote from the resection cavity or represented continued radiographic improvements in the residual tumor resection cavity without any further therapeutic intervention. Steroid doses were either unchanged or tapered during periods of clinical improvement.

Pathologic examination of tumor corresponding to loss of enhancement on MRI scans of Patients 2 and 3 demonstrated thrombosis of tumor blood vessels. Patient 2 showed striking loss of enhancement of the entire tumor and pathologic examination revealed a complete absence of endothelial proliferation-in the post-mortem specimen. Endothelial proliferation was broadly identified in pre-therapy tumor biopsy specimen from Patient 2. These findings raise the possibility that the radiologic response was related to loss of tumor vasculature attributable to this treatment.

Because of the inapparent toxicity and compelling responses, this treatment appears to yield an extraordinary therapeutic advantage as a biologic treatment of glioma. The responses described herein were obtained when the antisense-treated tumor cells were encapsulated in diffusion chambers constructed with 0.1 m pore-sized hydrophilic membranes. This exclusion limit excludes cells and suggests that soluble factors released by the antisense-treated cells could be responsible for triggering these responses.

A number of studies have documented lymphocytic infiltrates (LI) as a fairly common histologic feature of gliomas, but few have assessed L1 as a possible response to treatment. In one such study of 200 patients, histologic specimens from 28 documented cases of LI were reviewed for LI variations in successive biopsies obtained before and after intervening treatments such as radiation therapy. Eleven patients in this series revealed LI at initial biopsy with variable levels of LI at subsequent biopsies. Sixteen of 17 cases revealed absence of LI at initial biopsy with continued absence through all subsequent biopsies. In the current series, the much higher frequency of newly identified LI in post-treatment tumor tissues suggests a treatment-related effect when compared to results in this study. Previous studies have found a favorable correlation between perivascular LI and prognosis. In this series, three of the 4 patients with perivascular LI manifested clinical and radiographic improvement after treatment.

Selective tumor vessel thrombosis may represent a mechanism independent of an immune-mediated process. Tumor vessel thrombosis was observed in 6 of 6 evaluable patients treated, and although a different mechanism of selective tumor vessel thrombosis remains unclear, this response has been associated with an unambiguous tumor regression and associated clinical improvement in all of these patients. Similar tumor regressions have been observed in an animal model after selective occlusion of tumor vasculature.

The expected incidence of DVT in brain tumor patients is around 40%. In the pre-enoxaparin cohort, the incidence was 100% or 2.5-fold greater warranting enoxaparin prophylaxis. After enoxaparin treatment, the incidence dropped to 20%, or half the expected incidence, and in all cases without any associated hemorrhages. These findings are consistent with the safe and effective administration of enoxaparin in neurosurgical patients. Recent reports have reviewed the anti-thrombotic efficacy of enoxaparin in prospective randomized trials, and in one study a lower incidence of cancer-related mortality during the study period was shown. Despite this retrospective observation, a tumor lysis effect secondary to enoxaparin could be ruled out because responses were observed in three of the first four patients in whom enoxaparin treatment was not provided.

What is claimed is:

1. A method of inducing resistance to glioma tumor growth in a human comprising:
   (a) contacting a tumor cell in vitro or ex vivo with an oligonucleotide comprising SEQ ID NO:2, SEQ ID NO:3, SEQ ID NO:4, or SEQ ID NO:6; and
   (b) implanting a diffusion chamber containing said tumor cell into the rectus sheath of said human for a therapeutically effective time, thereby inducing resistance to glioma tumor growth.

2. The method of claim 1 wherein said therapeutically effective time is a time permitting death of said tumor cell in said diffusion chamber and permitting resistance of said tumor growth in said human.

3. The method of claim 1 wherein said tumor cell is excised from said human.

4. The method of claim 1 wherein said tumor cell is selected from cells from the group consisting of autografts, allografts, syngeneic, non-syngeneic, and xenografts.

5. The method of claim 1 wherein said tumor cell is selected from the group consisting of glioblastoma, pancreatic, melanoma, prostate, ovary, mammary, lungs, colon, and smooth muscle.

6. A method of inducing resistance to glioma tumor growth in a human comprising:
   contacting a tumor cell in vitro or ex vivo with an oligonucleotide comprising SEQ ID NO:3; and
   implanting a diffusion chamber containing said tumor cell into the rectus sheath of said human for a therapeutically effective time, thereby inducing resistance to glioma tumor growth.

7. A method of inducing resistance to glioma tumor growth in a human comprising:
   contacting a tumor cell in vitro or ex vivo with a vector that encodes an oligonucleotide comprising SEQ ID NO:2, SEQ ID NO:3, SEQ ID NO:4, or SEQ ID NO:6; and
   implanting a diffusion chamber containing said tumor cell into the rectus sheath of said human for a therapeutically effective time, thereby inducing resistance to glioma tumor growth.

8. A method of inducing regression of a glioma tumor in a human comprising:
   (a) contacting a tumor cell in vitro or ex vivo with an oligonucleotide comprising SEQ ID NO:2, SEQ ID NO:3, SEQ ID NO:4, or SEQ ID NO:6; and
   (b) implanting a diffusion chamber containing said tumor cell into the rectus sheath of said human for a therapeutically effective time, thereby inducing regression of said glioma tumor.

9. The method of claim 8 wherein said therapeutically effective time is a time permitting death of said tumor cell in said diffusion chamber and permitting regression of said tumor in said human.

10. The method of claim 8 wherein said tumor cell is excised from said human.

11. The method of claim 8 wherein said tumor cell is selected from cells from the group consisting of autografts, allografts, syngeneic, non-syngeneic, and xenografts.

12. The method of claim 8 wherein said tumor cell is selected from the group consisting of glioblastoma, pancreatic, melanoma, prostate, ovary, mammary, lungs, colon, and smooth muscle.

13. A method of inducing regression of a glioma tumor in a human comprising:

contacting a tumor cell in vitro or ex vivo with an oligonucleotide comprising SEQ ID NO: 3; and implanting a diffusion chamber containing said tumor cell into the rectus sheath of said human for a therapeutically effective time, thereby inducing regression of said glioma tumor.

14. A method of inducing regression of a glioma tumor in a human comprising:

contacting a tumor cell in vitro or ex vivo with a vector that encodes an oligonucleotide comprising SEQ ID NO:2, SEQ ID NO:3, SEQ ID NO:4, or SEQ ID NO:6; and implanting a diffusion chamber containing said tumor cell into the rectus sheath of said human for a therapeutically effective time, thereby inducing regression of said glioma tumor.

15. A method of inducing resistance to glioma tumor growth in a human comprising:

a) contacting a tumor cell in vitro or ex vivo with an oligonucleotide consisting of SEQ ID NO:3; and b) implanting a diffusion chamber containing said tumor cell into the rectus sheath of said human for a therapeutically effective time, thereby inducing resistance to glioma tumor growth.

* * * * *

UNITED STATES PATENT AND TRADEMARK OFFICE
CERTIFICATE OF CORRECTION

| | | |
|---|---|---|
| PATENT NO. | : 6,541,036 B1 | Page 1 of 1 |
| APPLICATION NO. | : 09/374712 | |
| DATED | : April 1, 2003 | |
| INVENTOR(S) | : David W. Andrews et al. | |

It is certified that error appears in the above-identified patent and that said Letters Patent is hereby corrected as shown below:

On page 11, col. 1, line 13-14 prior to "FIELD OF THE INVENTION", please insert the following:

--STATEMENT REGARDING FEDERALLY SPONSORED RESEARCH OR DEVELOPMENT

This invention was made with government support under contract number AG016522, AI034247 and CA060686 awarded by National Institutes of Health. The government has certain rights in the invention.--

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,541,036 B1 | Page 1 of 1 |
| APPLICATION NO. | : 09/374712 | |
| DATED | : April 1, 2003 | |
| INVENTOR(S) | : David W. Andrews et al. | |

It is certified that error appears in the above-identified patent and that said Letters Patent is hereby corrected as shown below:

Col. 1 prior to FIELD OF THE INVENTION, please insert the following:

--STATEMENT REGARDING FEDERALLY SPONSORED RESEARCH OR DEVELOPMENT

This invention was made with government support under contract numbers AG016522, AI034247 and CA060686 awarded by National Institutes of Health. The government has certain rights in the invention.--

Signed and Sealed this

Fifteenth Day of April, 2008

JON W. DUDAS
*Director of the United States Patent and Trademark Office*

SEQUENCE LISTING

<160> NUMBER OF SEQ ID NOS: 14

<210> SEQ ID NO 1
<211> LENGTH: 927

-continued

```
<212> TYPE: DNA
<213> ORGANISM: Homo sapien

<400> SEQUENCE: 1
cuuuguuuuc uuuucuuccu cacagaccuu cgggcaagga ccuucacaag        50
ggaugcagua caugcucugg cugccguugc ggaugaagcc cgagggcac        100 uccugcaugc acucgccguc guggaucaca aaccccucgg agucgcugcu       150
cucggcgcug aggauguugg cgcagaaguc acguccaca cagcgccagc        200 ccucaaaccu guaggguguug ggcgggcagg caggcacaca gacaccggca      250
uaguaguagu ggcggcaagc uacacaggcc gugucguugu caggcgcgcu       300
gcagcugccc aggcacucgg gguggcagca cucauuguuc ucggugcacg       350
cccgcuuccc acacgugcuu gggcacauuu ucuggcagcg guuugugguc       400
cagcagcggu aguuguacuc auuguugaug guggucuucu cacacaucgg       450
cuucuccucc auguucccug gacacagguc cccacauucc uuuggggcu        500 uauucccac aauguaguua uuggacaccg cauccaggau cagggaccag        550
uccacagugg agaguaaca gaggucagca uuuucacaa uccugauggc         600 cccccgagua auguuccuca gguuguaaag cccaauaucc uugagauugg       650
ucaucucgaa gaugaccagg gcguaguugu agaagaguuu ccagccgcgg       700
augaccguga gguuggggaa gaggucuccg aggcucucga ggccagccac       750
ucggaacagc agcaaguacu cgguaaugac cgugagcuug gggaagcggu       800
agcugcggua guccucggcc uuggagauga gcaggaugug gagguagccc       850
ucgaucaccg ugcaguucuc caggcgcuuc agcugcugau agucguugcg       900
gaugucgaug ccuggcccgc agauuuc                              927

<210> SEQ ID NO 2
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 2
tcctccggag ccagactt                                          18

<210> SEQ ID NO 3
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 3
ggaccctcct ccggagcc                                          18

<210> SEQ ID NO 4
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 4
ccggagccag acttcat                                           17
```

```
<210> SEQ ID NO 5
<211> LENGTH: 20
<212> TYPE: DNA
<213> ORGANISM: Artificial Sequence
<220> FEATURE:
<223> OTHER INFORMATION: antisense oligonucleotide

<400> SEQUENCE: 5
ctgctcctcc tctaggatga                                              20

<210> SEQ ID NO 6
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 6
ccctcctccg gagcc                                                   15

<210> SEQ ID NO 7
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 7
tacttcagac cgaggcc                                                 17

<210> SEQ ID NO 8
<211> LENGTH: 18
<212> TYPE: DNA
<213> ORGANISM: Artificial Sequence
<220> FEATURE:
<223> OTHER INFORMATION: antisense oligonucleotide

<400> SEQUENCE: 8
ccgaggcctc ctcccagg                                                18

<210> SEQ ID NO 9
<211> LENGTH: 9
<212> TYPE: PRT
<213> ORGANISM: Artificial Sequence
<220> FEATURE:
<223> OTHER INFORMATION: MHC class I-associated peptide

<400> SEQUENCE: 9

Tyr Leu Glu Pro Gly Pro Val Thr Ala
1               5

<210> SEQ ID NO 10
<211> LENGTH: 10
<212> TYPE: PRT
<213> ORGANISM: Artificial Sequence
<220> FEATURE:
<223> OTHER INFORMATION: MHC class I-associated peptide

<400> SEQUENCE: 10

Leu Leu Asp Gly Thr Ala Thr Leu Arg Leu
1               5                   10

<210> SEQ ID NO 11
<211> LENGTH: 9
<212> TYPE: PRT
<213> ORGANISM: Artificial Sequence
```

```
<220> FEATURE:
<223> OTHER INFORMATION: MHC class I-associated peptide

<400> SEQUENCE: 11

Phe Glu Cys Asn Thr Ala Gln Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: MHC class I-associated peptide

<400> SEQUENCE: 12

Ala Thr Val Pro Gly Pro Glu Leu Tyr
1               5

<210> SEQ ID NO 13
<211> LENGTH: 10
<212> TYPE: PRT
<213> ORGANISM: Artificial Sequence
<220> FEATURE:
<223> OTHER INFORMATION: MHC class I-associated peptide

<400> SEQUENCE: 13

Leu Arg Leu Thr Ala Thr Gly Asp Leu Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: MHC class I-associated peptide

<400> SEQUENCE: 14

Tyr Leu Arg Pro Gly Pro Val Thr Ala
1               5
```